United States Patent [19]

Asakura et al.

[11] Patent Number: 4,818,362

[45] Date of Patent: Apr. 4, 1989

[54] OXYGEN CONCENTRATION SENSING APPARATUS

[75] Inventors: Masahiko Asakura; Tomohiko Kawanabe; Minoru Muroya; Shin'ichi Kubota; Katsuhiko Kimura; Yasunari Seki; Kouji Matsuura, all of Wako, Japan

[73] Assignee: Honda Giken Kogyo Kabushiki Kaisha, Tokyo, Japan

[21] Appl. No.: 27,893

[22] Filed: Mar. 19, 1987

[30] Foreign Application Priority Data

Mar. 19, 1986 [JP] Japan .................................. 61-63201
Mar. 19, 1986 [JP] Japan .................................. 61-63199

[51] Int. Cl.$^4$ ........................................... G01N 27/58
[52] U.S. Cl. ................................. 204/406; 204/412; 204/425; 204/426
[58] Field of Search ............... 204/1 T, 406, 412, 410, 204/411, 425, 426

[56] References Cited

U.S. PATENT DOCUMENTS

| | | | |
|---|---|---|---|
| 4,440,621 | 4/1984 | Kitahara | 204/406 |
| 4,578,171 | 3/1986 | Yamada et al. | 204/406 |
| 4,586,476 | 5/1986 | Asayama | 123/440 |
| 4,594,139 | 6/1986 | Asayama et al. | 204/410 |
| 4,601,809 | 7/1986 | Kitahara | 204/406 |
| 4,609,452 | 9/1986 | Shimomura | 204/425 |
| 4,622,125 | 11/1986 | Oyama et al. | 204/425 |
| 4,622,126 | 11/1986 | Shimomura | 204/425 |
| 4,702,816 | 10/1987 | Hashimoto | 204/406 |

FOREIGN PATENT DOCUMENTS 8103410 3/1982 United Kingdom .

Primary Examiner—John F. Niebling
Assistant Examiner—Ben C. Hsing
Attorney, Agent, or Firm—Birch, Stewart, Kolasch & Birch

[57] ABSTRACT

An apparatus for sensing the concentration of oxygen in a gas such as engine exhaust gas includes an oxygen concentration sensor formed of an oxygen pump element and a sensor cell element, each based on a solid electrolytic member formed of a material such as $ZrO_2$, and is provided with a limiter circuit which functions to reduce the level of current supplied to the oxygen pump element when a voltage produced by the sensor cell element indicates that this current level is such as to produce a "blackening" phenomenon whereby deterioration of the oxygen pump element will occur and oxygen concentration sensing reliability will be lowered. The apparatus also includes a delay circuit which functions such that a reduction of the oxygen pump element current level is delayed by a predetermined time interval, after an increase of the sensor cell element voltage to the "blanking" region is detected, thereby preventing fluctuations in the oxygen pump element current level due to transient increases in sensor cell element voltage and increasing the sensing reliability.

7 Claims, 3 Drawing Sheets

OXYGEN CONCENTRATION SENSING APPARATUS

BACKGROUND OF THE INVENTION

1. Field of the Invention

The present invention relates to an oxygen concentration sensing apparatus for sensing the concentration of oxygen in a gas such as an engine exhaust gas.

2. Description of Background Information

An air/fuel ratio control apparatus is utilized to apply feedback control to the air/fuel ratio of a mixture which is supplied to an engine to hold the air/fuel ratio to a target value. This control is executed on the basis of the results of sensing the concentration of oxygen in the engine exhaust gas. Such air/fuel ratio control is employed in order to lower the level of pollutants in the exhaust gas, and also to lower the fuel consumption.

An oxygen concentration sensing apparatus which produces an output signal varying in proportion to the oxygen concentration within a gas under measurement has been developed for use in such an air/fuel ratio control apparatus (Japanese Patent Laid-open No. 58-153155). This oxygen concentration sensing apparatus employs an oxygen concentration sensor having a pair of oxygen ion-conductive solid electrolytic members, each in the form of a flat plate. These solid electrolytic members are disposed in the gas under measurement, with each of the solid electrolytic members having electrodes formed on a front and a rear face thereof, the solid electrolytic members being positioned mutually opposing, with a predetermined restricted region formed between them. One of the solid electrolytic members functions as an oxygen pump element, while the other functions as a sensor cell element for measuring the oxygen concentration ratio. If the oxygen concentration sensor is disposed within the gas which is under measurement, and a current is supplied to pass between the electrodes of the oxygen pump element with the direction of current flow being, for example, such that the electrode of the oxygen pump element which is in the restricted region becomes of negative polarity, then gaseous oxygen within the restricted region adjacent to that electrode of the oxygen pump element will become ionized and will flow through the oxygen pump element to be emitted from the positive electrode side of the oxygen pump element as gaseous oxygen. Variations in the concentration of gaseous oxygen within the restricted region will result in differences in oxygen concentration between the gas in the restricted region and the gas on the exterior of the oxygen concentration sensor, whereby a voltage is developed between the electrodes of the sensor cell element. If the level of the pump current supplied to the oxygen pump element is varied such as to mantain this voltage at a constant value, then assuming operation at constant temperature, the pump current value will vary substantially in a direct proportion to the concentration of oxygen within the gas which is under measurement, and an output proportional to this current is produced which represents an oxygen concentration sensing value.

With such an oxygen concentration sensing apparatus, if an excessively high level of pump current should flow through the oxygen pump element, then oxygen will be produced from the solid electrolytic member of the oxygen pump element itself. This results in a phenomenon referred to as "blackening". If for example the solid electrolytic members are formed of $ZrO_2$ (zirconium oxide), then when an excessively high level of pump current is supplied to the oxygen pump element, oxygen ($O_2$) will be produced from the $ZrO_2$, which will be converted to zirconium (Zr). This blackening phenomenon results in rapid deterioration of tne oxygen pump element, and causes reduced operating effectiveness of the oxygen concentration sensor. To prevent this phenomenon, therefore, it is necessary to hold the level of pump current at a value which is lower than a pump current region within which blackening occurs, this region being referred to in the following as the blackening phenomenon generation region.

FIG. 1 is a diagram showing the relationship between oxygen concentration and the pump current which is supplied to an oxygen pump element, with the voltage $V_S$ developed by the sensor cell element being a parameter. The diagram also indicates the blackening phenomenon generation region. The boundary of the blackening phenomenon generation region is linear, as is the relationship between pump current and oxygen concentration for a specific value of $V_S$ as a parameter, so that it is possible to judge from the value of $V_S$ whether or not the pump current value falls within the blackening phenomenon generation region. Thus, occurrence of the blanking phenomenon can be prevented by reducing the level of pump current whenever the voltage $V_S$ rises above a predetermined voltage, i.e. a voltage level indicating that operation is close to the blackening phenomenon generation region. However with such a method, if the voltage $V_S$ should rise above this predetermined level even momentarily, the pump current will be reduced. Immediately after $V_S$ has thereby been reduced below the predetermined level, the pump current will be increased. In this way the pump current level will fluctuate to such an extent that it will be impossible to reliably sense the oxygen concentration.

SUMMARY OF THE INVENTION

It is an objective of the present invention to provide an oxygen concentration sensing apparatus employing a method of sensing an oxygen concentration-proportional current, whereby occurrence of a blackening phenomenon can be prevented and whereby sensing of oxygen concentration can be reliably executed.

According to a first aspect, the present invention provides an oxygen concentration sensing apparatus whereby, when a voltage developed between electrodes of a sensor cell element increases above a predetermined voltage, a current which is supplied to an oxygen pump element is reduced after a predetermined time interval has elapsed.

According to a second aspect, the present invention provides an oxygen concentration sensing apparatus whereby, when a voltage developed between electrodes of a sensor cell element increases above a first predetermined voltage, a current which is supplied to an oxygen pump element is reduced after a predetermined time interval has elapsed, and whereby when the voltage developed between the electrodes of the sensor cell element has increased aoove the first predetermined voltage and then increases above a second predetermined voltage which is higher than the first predetermined voltage, the level of current supplied to the electrodes of the oxygen pump element is immediately substantially decreased or is halted.

An oxygen concentration sensing apparatus according to the present invention comprises an oxygen concentration sensor which includes a pair of oxygen ion-conductive solid electrolytic members disposed in a gas under measurement, each of the solid electrolytic members having a pair of electrodes formed thereon and said solid electrolytic members being disposed mutually opposing such as to form a restricted region, one of said pair of solid electrolytic members functioning as an oxygen pump element and the other functioning as a sensor cell element for measuring an oxygen concentration ratio, the oxygen concentration sensing apparatus further comprising current supply means for supplying a current which flows between the electrodes of the oxygen pump element at a level such that a constant voltage is maintained between the electrodes of the sensor cell element, and limiter means for limiting the level of current which is supplied to the electrodes of the oxygen pump element by the current supply means, with the level of current supplied to the electrodes of the oxygen pump element by the current supply means being produced by the apparatus as an oxygen concentration sensing voltage output, the limiter means including delay means whereby, when the voltage developed between the electrodes of the sensor cell element rises above a predetermined voltage, the level of current supplied to the oxygen pump element is reduced after a predetermined time interval has elapsed.

DETAILED DESCRIPTION OF EMBODIMENTS

Figure 1:
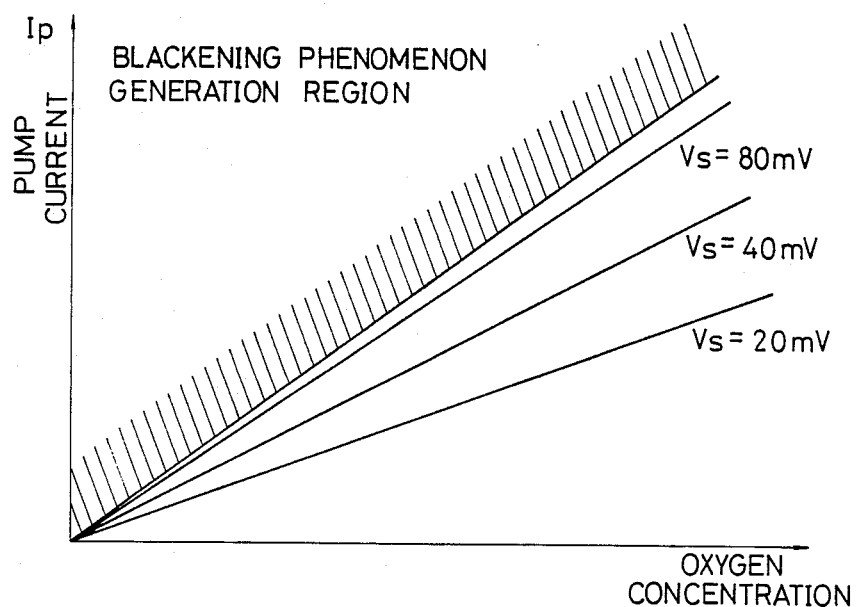
FIG. 1 is a diagram showing the relationship between oxygen concentration and pump current, and showing a blackening phenomenon generation region.
Figure 2:
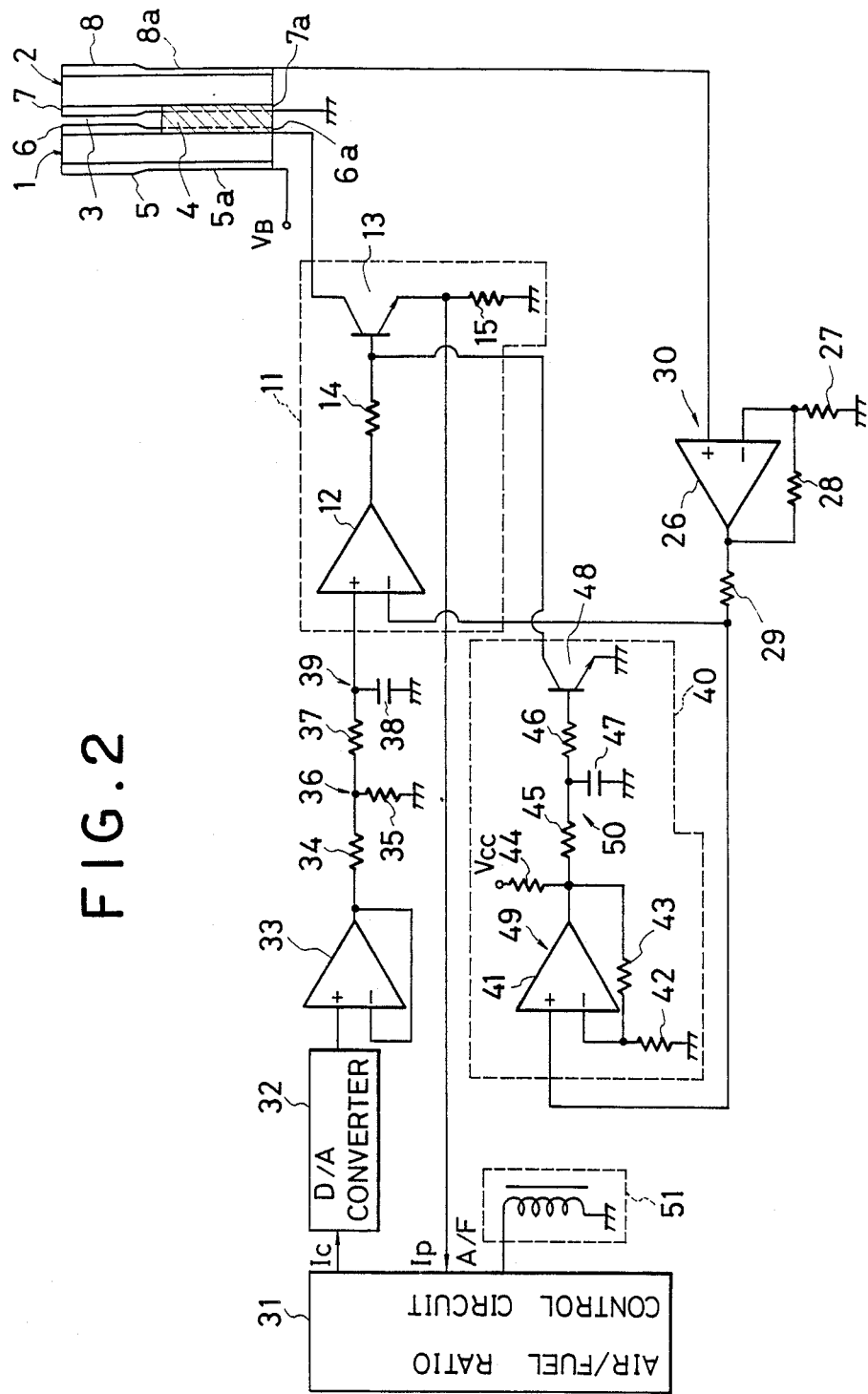
FIGS. 2 and 3 are circuit diagrams of respective embodiments of the present invention.

FIG. 2 shows an air/fuel ratio control apparatus which utilizes an oxygen concentration sensing apparatus according to the present invention. An oxygen concentration sensor made up of an oxygen pump element 1 and a sensor cell element 2, respectively formed as flat plate elements which are disposed mutually oposing, is mounted in the exhaust pipe (not shown in the drawings) of an engine. The main bodies of the oxygen pump element 1 and sensor cell element 2 are respectively formed of oxygen ion-conductive solid electrolytic members. A restricted region 3 is formed between respective ends of these solid electrolytic members, while the solid electrolytic members are mutually connected through a spacer 4 at the other ends thereof. Electrodes 5 tnrough 8, each formed of a porous heat-resistant metallic layer, are respectively formed on front and rear faces of one end of each of the oxygen pump element 1 and sensor cell element 2. Connecting leads 5a through 8a, respectively coupled to the electrodes 5 through 8, are respectively formed on the other ends of these faces of oxygen pump element 1 and sensor cell element 2.

A current is supplied from a current supply circuit 11 to flow between electrodes 5 and 6 of the oxygen pump element 1. The current supply circuit 11 consists of an operational amplifier 12, NPN transistor 13, and resistors 14 and 15. The output terminal of operational amplifier 12 is connected through resistor 14 to the base of transistor 13, while the emitter of transistor 13 is connected through resistor 15 to ground potential. Resistor 15 is provided in order to sense the level of pump current $I_P$ which flows between electrodes 5 and 6 of the oxygen pump element 1, and the voltage which is developed across resistor 15 is supplied to an $I_P$ input terminal of an air/fuel ratio control circuit 31 as a current value $I_P$. The collector of transistor 13 is connected through the connecting lead 6a to the inner electrode 6 of oxygen pump element 1, while a voltage $V_B$ is applied through connecting lead 5a to the outer electrode 5 of oxygen pump element 1.

The inner electrode 7 of sensor cell element 2 is connected through the connecting lead 7a to ground potential, while the outer electrode 8 is connected through connecting lead 8a to the input of a non-inverting inverting amplifier 30 which is formed of an operational amplifier 26 and resistors 27 through 29. The output terminal of the non-inverting amplifier 30 is connected to the inverting input terminal of operational amplifier 12.

An $I_C$ control output terminal of the air/fuel ratio control circuit 31 is connected to a D/A converter 32. The D/A converter 32 produces an output voltage in response to a digital signal which appears on the $I_C$ control output terminal of air/fuel ratio control circuit 31. The output terminal of D/A converter 32 is connected through a voltage follower circuit 33, formed of an operational amplifier, through a voltage-divider circuit 36 consisting of resistors 34 and 35, and through a integrator circuit 39 formed of a resistor 37 and a capacitor 38, to the non-inverting input terminal of operational amplifier 12.

The output terminal of the non-inverting amplifier 30 is connected to a limiter circuit 40, which is formed of an operational amplifier 41, resistors 42 through 46, a capacitor 47, and an NPN transistor 48. The operational amplifier 41 and resistors 42 and 43 form a non-inverting amplifier 49. A voltage $V_{CC}$ is supplied through resistor 44 to the output terminal of non-inverting amplifier 49, while in addition the output terminal of amplifier 49 is connected to an integrator circuit 50 which is formed of a resistor 45 and a capacitor 47. The output terminal of integrator circuit 50 is connected through a resistor 46 to the base of transistor 48. The emitter of transistor 48 is connected to ground potential, and the collector is connected to the base of transistor 13.

In addition to the $I_C$ and $I_P$ terminals, the air/fuel ratio control circuit 31 also includes an A/F drive terminal, which is connected to an electromagnetic valve 51 utilized for adjustment of a secondary air supply. The electromagnetic valve 51 is mounted in a secondary air intake passage which communicates with the air intake passage of the engine, downstream from the throttle valve.

The operation of the apparatus described above is as follows. When a digital signal is supplied from the $I_C$ output temminal of air/fuel ratio control circuit 31 to D/A converter 32, the signal is converted to a voltage, which is supplied through the voltage follower 33 to the voltage divider 36. The output voltage from voltage follower 33 is thereby voltage-divided, by a division ratio which is determined by the values of resistors 34 and 35, and the voltage-divided output from divider 36 is applied to integrator circuit 39. The output voltage from integrator circuit 39 gradually rises to attain the level of the output voltage from voltage divider 36, in accordance with an integration time constant which is determined by the values of resistor 37 and capacitor 38, and so varies in a stable manner. This output voltage from integrator circuit 39 is supplied as a reference voltage $V_{r1}$ to the non-inverting input terminal of operational amplifier 12. When this reference voltage $V_{r1}$ begins to be supplied, the voltage level at the inverting input terminal of operational amplifier 12 is lower than $V_{r1}$, and hence the output level from operational amplifier 12 will be at a high (positive) level, so that transistor 13 will be set in the ON state. As a result, pump current will flow between electrodes 5 and 6 of oxygen pump element 1.

Due to this flow of pump current, a voltage $V_S$ is developed between the electrodes 7 and 8 of sensor cell element 2, and is supplied to the non-inverting amplifier 30, to be amplified thereby. The amplified voltage is supplied to the inverting input terminal of operational amplifier 12. When voltage $V_S$ rises, the output voltage $V_S'$ from the non-inverting amplifier 30 also rises. When this output voltage $V_S'$ exceeds the reference voltage $V_{r1}$, the output voltage from operational amplifier 12 falls to a low level, whereby transistor 13 is set in the OFF state. Due to this OFF state of transistor 13, the level of pump current is reduced, so that the voltage $V_S$ developed between electrodes 7 and 8 of sensor cell element 2 is reduced, whereby the voltage $V_S'$ supplied to the inverting input terminal of operational amplifier 12 from non-inverting amlifier 26 is also reduced. When voltage $V_S'$ falls below the reference voltage $V_{r1}$, the output from operational amplifier 12 again rises to the high level, whereby the level of pump current flow is increased. Since the above sequence of operation is executed repetitively at high speed, the voltage $V_S$ is controlled to maintain a constant level, which is determined by a value expressed by the digital signal from air/fuel ratio control circuit 31.

While the reference voltage $V_{r1}$ is being supplied to operational amplifier 12, the level $I_P$ of the pump current which flows between electrodes 5 and 6 of oxygen pump element 1 is sensed as a voltage which is developed across resistor 15, and this voltage is supplied to the $I_P$ input terminal of air/fuel ratio control circuit 31. The air/fuel ratio control circuit 31 thereby judges whether or not the pump current value $I_p$ is lower than a reference value $I_r$, which corresponds to a target value of air/fuel ratio. If $I_p < I_r$, then this is taken as indicating that the air/fuel ratio of the mixture supplied to the engine is rich, and therefore the electromagnetic valve 51 is driven in an opening direction, to thereby supply secondary air to the engine. If $I_p \geq I_r$, then this is taken as indicating that the air/fuel ratio of the mixture is lean, and therefore driving of the electromagnetic valve 51 to the open position is halted, thereby halting the supply of secondary air to the engine.

If the voltage $V_S$ developed between electrodes 7 and 8 of sensor cell element 2 rises, then the output voltge $V_S'$, from non-inverting amplifier 30 also rises. $V_S'$ is amplified by non-inverting amplifier 49, and the resultant amplified voltage is supplied to integrator circuit 50. The output voltage from integrator circuit 50 is transferred through resistor 46 to the base of transistor 48. If the output voltage $V_S'$ should suddenly increase, then the output voltage from integrator circuit 50 will only increase gradually. If the output voltage from 49 exceeds the reference voltage $V_{r1}$, i.e. exceeds a predetermined voltage level (for example 60 mV), then transistor 48 will be set in the ON state. This will occur after a time delay $t_1$ has elapsed following the sudden increase of voltage $V_S'$. Since the potential of the base of transistor 13 is brought close to ground potential by the ON (i.e. saturated) state of transistor 48, transistor 13 will be set in the OFF state, and the flow of pump current will be reduced. Thus if the output voltage $V_S'$ from non-inverting amplifier 30 rises to a level which is close to the blackening phenomenon generation region, the output voltage from integrator circuit 50 will gradually increase, and after a delay time $t_1$ has elapsed (immediately before the blackening phenomenon generation region is reached), the pump current will be reduced.

In the embodiment of the present invention described above, an integrator circuit formed of a capacitor and a resistor is utilized as delay means, however any integrator circuit could be employed, for example, are formed of a resistor and an inductor.

Figure 3:
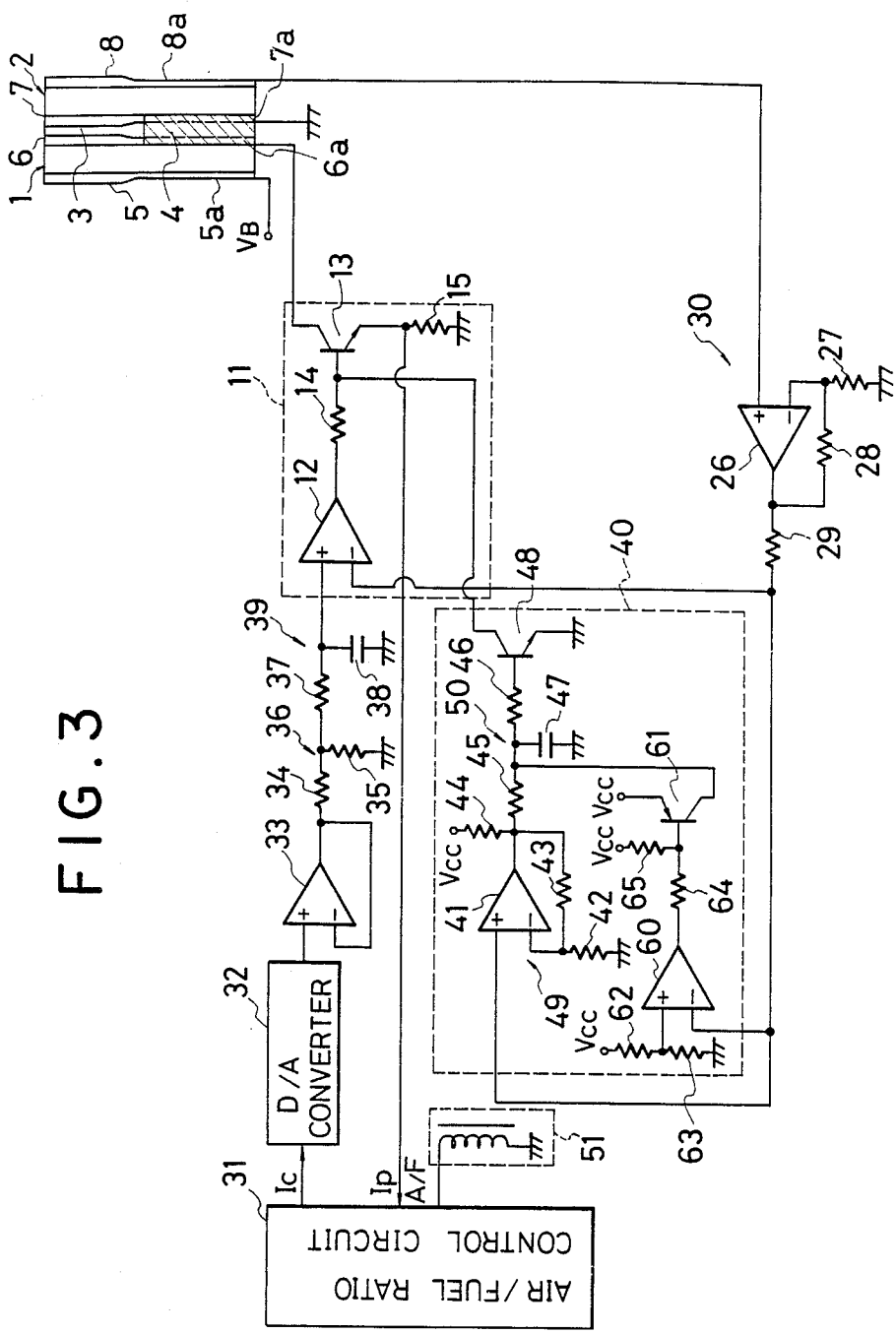

FIG. 3 shows a second embodiment of an air/fuel ratio control apparatus which utilizes an oxygen concentration sensing apparatus according to the present invention. This air/fuel ratio control apparatus is identical to that of FIG. 2, with the exception of an operational amplifier 60, a PNP transistor 61, and resistors 62 to 65 wnich are added to the limiter circuit 40. The operational amplifier 60 functions as a comparator which compares the output voltage from non-inverting amplifier 30 with a voltage produced by voltage division of $V_{CC}$ by resistors 62 and 63. The output terminal of operational amplifier 60 is coupled through resistor 64 to the base of PNP transistor 61, while the base of transistor 61 is also connected through resistor 65 to voltage $V_{CC}$. The emitter of transistor 61 is connected directly to voltage $V_{CC}$, while the collector is connected to the output of integrator circuit 50, i.e. to the common connection point of resistor 46 and capacitor 47.

If the voltage $V_S$ developed between electrodes 7 and 8 of sensor cell element 2 rises, then the output voltage $V_S'$ from non-inverting amplifier 30 also rises. $V_S'$ is amplified by non-inverting amplifier 49, and the resultant amplified voltage is supplied to integrator circuit 50. The output voltage from integrator circuit 50 is transferred through resistor 46 to the base of transistor 48. If the output voltage $V_S'$ should suddenly increase, then the output voltage from integrator circuit 50 will only increase gradually. If the output voltage from 49 exceeds the reference voltage $V_{r1}$, i.e. exceeds a predetermined voltage level (for example 60 mV), then transistor 48 will be set in the ON state. This will occur after a time delay $t_1$ has elapsed following the sudden increase of voltage $V_S'$. Since the potential of the base of transistor 13 is reduced or is brought close to ground potential by the ON (i.e. saturated) state of transistor 48, transistor 13 will be set in a condition of reduced conductance between collector and emitter, or will be set in the OFF state, and the flow of pump current will be reduced or will be halted. Thus if the output voltage $V_S'$ from non-inverting amplifier 30 rises to a level which is close to the blackening phenomenon generation region, the output voltage from integrator circuit 50 will gradually increase, and after a delay time $t_1$ has elapsed (immediately before the blanking phenomenon generation region is reached), the flow of pump current will be reduced or interrupted.

If the pump current should reach the blackening phenomenon generation region and should thereafter continue to increase, then voltage $V_S$ will exceed a second predetermined voltage (for example 80 mV). When this occurs, the output voltage $V_S'$ from non-inverting amplifier 30 will exceed the voltage-divided output level from resistors 62 and 63, so that the output from operational amplifier 60 will be inverted from the high to the low level. Current will therefore flow into the base of transistor 61, at a value determined by resistors 64 and 65, so that transistor 61 will be set in the ON state. Due to this ON state of transistor 61, voltage $V_{CC}$ will be applied through the emitter and collector of transistor 61 to the capacitor 47 of integrator circuit 50, whereby capacitor 47 will be charged at a more rapid rate than by charging resulting from the rise in output voltage from non-inverting amplifier 49. Thus, when $V_S'$ rises above the voltage-divided output from resistors 62, 63, the voltage across capacitor 47 is rapidly increased, thereby setting transistor 48 in the ON state. is a result, the potential of the base of transistor 13 falls, whereby transistor 13 enters a state of low conduction and the flow of pump current is reduced or interrupted. In this way when the pump current level rises to the blackening phenomenon generation region, that current is immediately reduced.

In the second embodiment of the present invention described above, an integrator circuit formed of a capacitor and a resistor is utilized as delay means, however it would be equally possible to employ any integrator circuit, for example one formed of a resistor and an inductor.

In the embodiments described above, the potential of the base of transistor 13 is brought substantially close to ground potential when transistor 48 is set in the ON state, to thereby reduce the pump current and prevent occurrence of the blackening phenomenon. However it would be equally possible to reduce the pump current by increasing the voltage level at the inverting input terminal of operational amplifier 12 above the level of the non-inverting input of operational amplifier 12.

Thus as described in the above, the present invention provides an oxygen concentration sensing apparatus whereby, when a voltage developed between the electrodes of a sensor cell element exceeds a predetermined voltage, then after a predetermined time interval has elapsed, the pump current is reduced to thereby prevent the occurrence of a blackening phenomenon, and so prevent rapid deterioration of the oxygen pump element. Furthermore in the event that the voltage developed between the electrodes of the sensor cell element increases above a predetermined voltage only momentarily, i.e. above a predetermined voltage below which the blackening phenomenon will not occur, reduction of the pump current is prevented. In this way, fluctuations of the pump current level can be eliminated, and the reliability of sensing the oxygen concentration can be increased.

With an oxygen concentration sensing apparatus employing a method of sensing an oxygen concentration-proportional current according to the present invention, a current which is supplied to flow between the electrodes of an oxygen pump element is only reduced, after a time interval has elapsed following an increase in the voltage developed between the electrodes of a sensor cell element above a first predetermined voltage. In this way, the occurrence of a blackening phenomenon which results in rapid deterioration of the oxygen pump element is prevented. Furthermore, if the voltage which is developed between the electrodes of the sensor cell element should approach a value corresponding to the blackening phenomenon generation region only momentarily, the method of the present invention inhibits reduction of pump current, thereby avoiding fluctuations in the pump current level. The reliability of sensing by the oxygen concentration sensing apparatus is thereby enhanced, by comparison with the prior art. In addition, if the voltage which is developed between the electrodes of the sensor cell element should rise above the first predetermined voltage and then exceed a second predetermined voltage, the supply of current between the electrodes of the oxygen pump element is substantially immediately reduced, so that the apparatus can respond to a sudden increase in the pump current into the blackening phenomenon generation region. In this way, occurrence of the blackening phenomenon can be reliably prevented.

What is claimed is:

1. An oxygen concentration sensing apparatus comprising:
   oxygen sensing means including,
      first and second oxygen ion-conductive solid electrolytic members disposed in a gas under measurement, each of said first and second solid electrolytic members having a pair of electrodes formed thereon, said first and second solid electrolytic members being disposed apart so as to form a restricted region therebetween, said first solid electrolytic member functioning as an oxygen pump element and said second solid electrolyte member functioning as a sensor cell element for measuring an oxygen concentration ratio;
   current supply means for supplying a current between said electrodes of said oxygen pump element at a level such that a constant voltage is maintained between said electrodes of said sensor cell element; and
   limiter means for limiting said level of said current supplied by said current supply means,
   said current supply means developing an oxygen concentration sensing voltage output proportional to said level of said current supplied to said oxygen pump element;
   said limiter means including delay means for controlling said limiter means to reduce said level of current supplied to flow between said electrodes of said oxygen pump element after a predetermined time interval has elapsed after the voltage developed between said electrodes of said sensor cell element increases above a predetermined voltage.

2. An oxygen concentration sensing apparatus according to claim 1, in which said delay means reduces said level of current supplied to flow between said electrodes of said oxygen pump element after a predetermined time interval has elapsed from when the voltage developed between said electrodes of said sensor cell element increase above a first predetermined voltage, said limiter means including switch means responsive to an increases of said voltage developed between said electrodes of said sensor cell element above a second predetermined voltage which is greater than said first predetermined voltage, for immediately reducing said level of current.

3. An oxygen concentration sensing apparatus according to claim 2, in which said switch means functions to halt operation of said delay means when said voltage developed between said electrodes of said sensor cell element increases above said second predetermined voltage.

4. An oxygen concentration sensing apparatus according to claim 3, in which said delay means comprises a charging circuit and in which said switch means functions to rapidly charge said charging circuit when said voltage developed between said electrodes of said sensor cell element increases above said second predetermined voltage.

5. An oxygen concentration sensing apparatus comprising:
    oxygen sensing means for sensing oxygen in a gas under measurement and producing an output signal having a magnitude proportional to the concentration of oxygen in said gas unter measurement, said oxygen sensor means including,
        a sensor cell element having a first active plate and a first pair of electrodes sandwiching said first active plate, and
        an oxygen pump element having a second active plate and a second pair of electrodes sandwiching said second active plate,
        said first and second active plates defining a restricted region into which said gas to be measured is introduced;
    command generating means for generating a voltage valve command, said voltage value command representing a voltage to be generated across said first pair of electrodes of said sensor cell element;
    current supply means, responsive to said voltage value command, for supplying a pump current across said second pair of electrodes of said oxygen pump element so that a voltage being generated across said first pair of electrodes of said sensor cell element equals said voltage represented by said voltage value command, said current supply means developing a current value of said pump current as said output signal indicating measured oxygen concentration; and
    limit means, responsive to said voltage generated across said first pair of electrodes of said sensor cell element, for limiting the level of said current supplied by said current supply means, said limit means including,
        first means for determining if said voltage generated across first pair of electrodes of said sensor cell element has exceeded a first predetermined voltage level and developing an excess voltage detection output,
    delay means, responsive to said detection output, for developing a first current inhibit output a delayed time after receipt of said excess voltage detection output, and
    means for reducing the supply of pump current to said oxygen pump element by said current supply means in response to said first current inhibit output.

6. The sensing apparatus of claim 5 wherein said limit means includes second means for determining if said voltage generated across said first pair of electrodes of said sensor cell element has exceeded a second predetermined voltage higher than said first predetermined voltage and for substantially immediately developing a second current inhibit output,
    said means for reducing being also responsive to said second current inhibit output to reduce the supply of pump current to said oxygen pump element.

7. The sensing apparatus of claim 5 wherein said gas under measurement is the exhaust of an internal combustion engine.

* * * * *